(12) United States Patent
Tassoni, Jr. et al.

(10) Patent No.: US 11,844,909 B2
(45) Date of Patent: Dec. 19, 2023

(54) GUIDE CATHETER WITH REINFORCING MEMBER

(71) Applicant: BOSTON SCIENTIFIC SCIMED, INC., Maple Grove, MN (US)

(72) Inventors: Anthony Frank Tassoni, Jr., Andover, MN (US); Timothy Lawrence Rubesch, Blaine, MN (US); Henry J. Pepin, Loretto, MN (US); Ajay Gupta, Shoreview, MN (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 0 days.

(21) Appl. No.: 17/199,246

(22) Filed: Mar. 11, 2021

(65) Prior Publication Data

US 2021/0290896 A1   Sep. 23, 2021

Related U.S. Application Data

(60) Provisional application No. 62/993,476, filed on Mar. 23, 2020.

(51) Int. Cl.
*A61M 25/00* (2006.01)
(52) U.S. Cl.
CPC ...... *A61M 25/005* (2013.01); *A61M 25/0012* (2013.01)
(58) Field of Classification Search
CPC ............ A61M 25/005; A61M 25/0012; A61M 25/0053; A61M 25/0054
See application file for complete search history.

(56) References Cited

U.S. PATENT DOCUMENTS

| | | | |
|---|---|---|---|
| 5,002,041 A | | 3/1991 | Chikama |
| 5,037,404 A | * | 8/1991 | Gold ................. A61M 25/0012 604/527 |
| 6,143,013 A | | 11/2000 | Samson et al. |
| 6,217,565 B1 | * | 4/2001 | Cohen ................. A61M 25/005 604/525 |
| 6,648,874 B2 | | 11/2003 | Parisi et al. |

(Continued)

FOREIGN PATENT DOCUMENTS

| | | |
|---|---|---|
| CN | 102247223 A | 11/2011 |
| EP | 0369383 A1 | 5/1990 |

(Continued)

OTHER PUBLICATIONS

International Search Report and Written Opinion dated Aug. 30, 2021 for International Application No. PCT/US2021/021995.

*Primary Examiner* — Laura A Bouchelle
*Assistant Examiner* — John A Doubrava
(74) *Attorney, Agent, or Firm* — Seager, Tufte & Wickhem, LLP

(57) ABSTRACT

Example medical devices are disclosed. An example medical device includes an elongate member having a proximal end region, a distal end region and an outer surface. The medical device also includes a plurality of filaments braided together in a first braided pattern along a first braided region of the elongate member, wherein the plurality of filaments extend continuously to a second braided region along the elongate member, wherein the plurality of filaments along the second braided region form a second braided pattern different from the first braided pattern.

19 Claims, 10 Drawing Sheets

(56) References Cited

U.S. PATENT DOCUMENTS

| | | |
|---|---|---|
| 6,669,886 B1 | 12/2003 | Willard |
| 6,929,626 B2 | 8/2005 | Dicarlo et al. |
| 7,413,543 B2 | 8/2008 | Banik et al. |
| 7,569,046 B2 | 8/2009 | Zhou |
| 7,578,786 B2 | 8/2009 | Boulais et al. |
| 7,591,783 B2 | 9/2009 | Boulais et al. |
| 7,824,392 B2 * | 11/2010 | Zhou ................. A61M 25/0053 604/523 |
| 7,922,650 B2 | 4/2011 | Mcweeney et al. |
| 8,118,732 B2 | 2/2012 | Banik et al. |
| 8,425,408 B2 | 4/2013 | Boulais et al. |
| 8,475,366 B2 | 7/2013 | Boulais et al. |
| 8,535,219 B2 | 9/2013 | Smith et al. |
| 8,608,648 B2 | 12/2013 | Banik et al. |
| 8,608,649 B2 | 12/2013 | McWeeney et al. |
| 8,636,270 B2 | 1/2014 | Ostrovsky |
| 8,715,270 B2 | 5/2014 | Weitzner et al. |
| 2004/0089969 A1 | 5/2004 | Willard |
| 2004/0143159 A1 | 7/2004 | Wendlandt |
| 2005/0080449 A1 | 4/2005 | Mulder |
| 2005/0119527 A1 | 6/2005 | Banik et al. |
| 2005/0131279 A1 | 6/2005 | Boulais et al. |
| 2005/0245789 A1 | 11/2005 | Smith et al. |
| 2007/0255255 A1 * | 11/2007 | Shah .................... A61M 25/005 604/527 |
| 2008/0252046 A1 * | 10/2008 | Bradburn .............. B60R 21/235 280/728.1 |
| 2008/0262472 A1 | 10/2008 | Lunn et al. |
| 2010/0217184 A1 | 8/2010 | Koblish et al. |
| 2012/0004502 A1 | 1/2012 | Weitzner et al. |
| 2012/0123327 A1 | 5/2012 | Miller |
| 2012/0209073 A1 | 8/2012 | McWeeney et al. |
| 2012/0277671 A1 | 11/2012 | Fuentes |
| 2013/0026740 A1 * | 1/2013 | Finn ....................... D06C 15/02 28/169 |
| 2013/0172879 A1 | 7/2013 | Sutermeister et al. |
| 2013/0261396 A1 | 10/2013 | Boulais et al. |
| 2013/0289352 A1 | 10/2013 | Boulais et al. |
| 2014/0066706 A1 | 3/2014 | McWeeney et al. |
| 2014/0073852 A1 | 3/2014 | Banik et al. |
| 2018/0243530 A1 * | 8/2018 | Lederman .............. A61B 5/055 |

FOREIGN PATENT DOCUMENTS

| | | |
|---|---|---|
| EP | 2397108 A2 | 12/2011 |
| WO | 9807523 A1 | 2/1998 |
| WO | 2008031103 A2 | 3/2008 |

* cited by examiner

GUIDE CATHETER WITH REINFORCING MEMBER

CROSS-REFERENCE TO RELATED APPLICATIONS

This application claims the benefit of priority under 35 U.S.C. § 119 to U.S. Provisional Application Ser. No. 62/993,476, filed Mar. 23, 2020, the entirety of which is incorporated herein by reference.

TECHNICAL FIELD

The present disclosure pertains to medical devices, and methods for manufacturing medical devices. More particularly, the present disclosure pertains to elongated intracorporeal medical devices including a tubular member connected with other structures, and methods for manufacturing and using such devices.

BACKGROUND

The use of intracorporal medical devices, such as intravascular catheters, guidewires, or the like, has become an effective method for treating many types of disease. For example, in some treatments, an intracorporeal device may be inserted into the anatomy, such as the vascular system, of a patient and navigated to a desired target site, where it can be used in treating the target site. Using this method, various target sites in the patient's anatomy can be accessed, including the coronary, cerebral, and peripheral vasculature, for example. Examples of therapeutic purposes for intravascular devices include percutaneous transluminal angioplasty (PTA) and percutaneous transluminal coronary angioplasty (PTCA).

In some devices, such as guide catheters, a reinforcing member, such as a braided filament, may be disposed along and/or within the catheter shaft. The reinforcing member be designed to affect various performance characteristics of the catheter. For example, the reinforcing member may be utilized to influence the kink, torque, stiffness, burst pressure, tensile strength, outside diameter, elongation, etc. of the catheter. Further, in some instances it may be desirable to customize different portions of the catheter to have different performance characteristics. For example, it may be desirable to design a guide catheter to have increased flexibility on its distal end region relative to its proximal end region. Additionally, in some instances, a particular braid pattern of a reinforcing member may affect the performance characteristics of the catheter. Therefore, it may desirable to design a catheter having a reinforcing member arranged in different braid patterns along and/or within the catheter's shaft. There is an ongoing need to design and manufacture guide catheters having variable reinforcing braid patterns to customize the particular performance characteristics of the guide catheters.

BRIEF SUMMARY

This disclosure provides design, material, manufacturing method, and use alternatives for medical devices. An example medical device includes an elongate member having a proximal end region, a distal end region and an outer surface. The medical device also includes a plurality of filaments braided together in a first braided pattern along a first braided region of the elongate member, wherein the plurality of filaments extend continuously to a second braided region along the elongate member, wherein the plurality of filaments along the second braided region form a second braided pattern different from the first braided pattern.

Alternatively or additionally to any of the embodiments above, wherein the plurality of filaments continuously transition from the first braided pattern to the second braided pattern along a transition region.

Alternatively or additionally to any of the embodiments above, wherein the transition region includes a length between 0.040 inches and 0.060 inches.

Alternatively or additionally to any of the embodiments above, wherein the filaments forming the first braided pattern are interwoven in a diamond-half load braid pattern.

Alternatively or additionally to any of the embodiments above, wherein the filaments forming the first braided pattern are interwoven in a herringbone braid pattern.

Alternatively or additionally to any of the embodiments above, wherein the plurality of filaments of the first braided region define a first pitch angle, and wherein the plurality filaments of the second braided region define a second pitch angle different from the first pitch angle.

Alternatively or additionally to any of the embodiments above, wherein a first filament of the plurality of filaments extends parallel to a second filament of the plurality of filaments to form a first pair of filaments in the second braided region.

Alternatively or additionally to any of the embodiments above, wherein a third filament of the plurality of filaments extends parallel to a fourth filament of the plurality of filaments to form a second pair of filaments in the second braided region.

Alternatively or additionally to any of the embodiments above, wherein the first pair of filaments is interwoven with the second pair of filaments in the second braided region.

Alternatively or additionally to any of the embodiments above, wherein the first pair of filaments is interwoven with the second pair of filaments in diamond-full load braid pattern.

Alternatively or additionally to any of the embodiments above, wherein the plurality of filaments are disposed along the outer surface of the elongate tubular member.

An example guide catheter includes an elongate shaft having a lumen, an outer surface and a plurality of reinforcing wires disposed along the outer surface. Further, the plurality of reinforcing wires are interwoven in a first braided pattern along a first braided region of the elongate shaft, wherein the plurality of reinforcing wires extend continuously to a second braided region, and wherein the plurality of reinforcing wires of the second braided region form a second braided pattern different from the first braided pattern.

Alternatively or additionally to any of the embodiments above, wherein the plurality of reinforcing wires continuously transition from the first braided pattern to the second braided pattern along a transition region.

Alternatively or additionally to any of the embodiments above, wherein the reinforcing wires forming the first braided pattern are interwoven in a diamond-half load braid pattern.

Alternatively or additionally to any of the embodiments above, wherein the reinforcing wires forming the first braided pattern are interwoven in a herringbone braid pattern.

Alternatively or additionally to any of the embodiments above, wherein a first wire of the plurality of reinforcing wires extends parallel to a second wire of the plurality of reinforcing wires to form a first pair of wires in the second braided region.

Alternatively or additionally to any of the embodiments above, wherein a third wire of the plurality of wires extends parallel to a fourth wire of the plurality of reinforcing wires to form a second pair of wires in the second braided region.

Alternatively or additionally to any of the embodiments above, wherein the first pair of wires is interwoven with the second pair of wires in the second braided region.

Alternatively or additionally to any of the embodiments above, wherein the first pair of filaments is interwoven with the second pair of filaments in diamond-full load braid pattern.

An example method of manufacturing a guide catheter includes attaching a plurality of wires to an outer surface of an elongate member, wherein the plurality of wires forms a first braided pattern along a first braided region of the elongate member, and wherein the plurality of wires forms a second braided pattern along a second braided region of the elongate member, wherein the second braided pattern is different from first braided pattern, and wherein the plurality of wires extends continuously from the first braided region to the second braided region.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The disclosure may be more completely understood in consideration of the following detailed description in connection with the accompanying drawings, in which.

Figure 1:
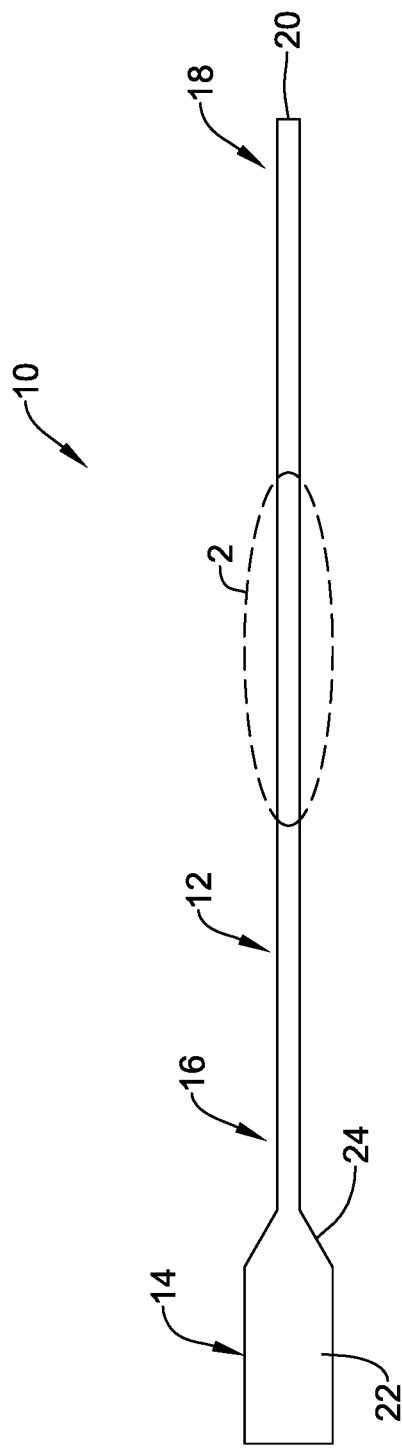
FIG. 1 illustrates an example guide catheter.

While the disclosure is amenable to various modifications and alternative forms, specifics thereof have been shown by way of example in the drawings and will be described in detail. It should be understood, however, that the intention is not to limit the disclosure to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (e.g., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used connection with other embodiments whether or not explicitly described unless clearly stated to the contrary.

The following detailed description should be read with reference to the drawings in which similar elements in different drawings are numbered the same. The drawings, which are not necessarily to scale, depict illustrative embodiments and are not intended to limit the scope of the disclosure.

FIG. 1 is a plan view of an example elongated medical device, such as a guide catheter 10 or the like. The catheter 10 may include a shaft 12 having a proximal end region 16, a distal end region 18, and may include one or more lumens 20 extending therethrough. The catheter shaft 12 can be manufactured to provide specific, desired characteristics of the catheter 10, depending upon the intended use. For example, the shaft 12 may be designed to maintain a desired level of flexibility, torquability, column strength, trackability, outside diameter, tensile strength, elongation, etc. appropriate for maneuvering the catheter 10 through the vasculature of a patient.

In some embodiments, the shaft 12 of the catheter 10 may be characterized as a tubular member that includes one or more lumens 20 extending a portion of or the entire length of the shaft 12. The one or more lumens 20 extending within the shaft 12 may include an inner diameter capable of transmitting fluids, or in some cases, receiving another medical device, such as a guidewire, catheter (e.g., a diagnostic catheter), a balloon catheter, a stent delivery catheter, a distal protection device, other device, or the like. As can be appreciated, the shaft 12 may include any of a wide variety of sizes, structures, layers, and/or materials that may be adapted for the particular usage intended for the catheter, some examples of which are described herein.

A hub assembly (e.g., manifold structure) 14 may be disposed adjacent to the proximal region 16 of the shaft 12. The hub assembly 14 may include a hub portion 22, and a strain relief portion 24 that may be adapted and/or configured, for example, to provide for a transition in flexibility characteristics between that of the hub portion 22 and the shaft 12, and may ease the transition from the catheter shaft 12 to the hub portion 22. The hub portion 22 may include one or more ports in fluid communication with the shaft 12 and may provide for and/or define a pathway through to the lumen 20 within the shaft 12. The pathway may, for example, allow for a medical device, such as a guidewire or the like, to extend through the hub portion 22 and into the shaft 12. Additionally, and/or alternatively, the pathway may provide a path for fluid (e.g., contrast medium, medicaments, saline, an inflation fluid, or the like) to enter the shaft 12.

In other embodiments, the hub portion 22 may include a plurality of ports that may provide for and/or define a pathway to multiple lumens within the shaft 12. The hub portion 22 may also include an outer surface that includes features configured to allow for gripping and/or manipulation of the hub portion 22. For example, the hub portion 22 may include one or more features that may aid in facilitating manipulation of the catheter 10 during navigation within the anatomy. For example, the hub portion 22 may include wings, protrusions, widened portions, surface texture, etc. having any of a wide variety or geometries that may aid the physician in gripping and/or manipulating the hub portion 22 when the physician urges and/or navigates the catheter 12 by applying longitudinal and/or torsional forces to the hub portion 22.

In some examples, the shaft 12 may be constructed using a plurality of components or layers. For example, in some embodiments, the shaft 12 may have two, three, four or more layers. Multiple layers may impart desirable characteristics to the shaft 12. For example, in some embodiments, an inner layer may be made of a lubricious material designed to ease the insertion and/or advancement of other medical devices through the lumen 20.

In other examples, the catheter shaft 12 may include a reinforcing layer, such as a braid (e.g., a braided filament), designed to provide desirable characteristics, such as specific flexibility and/or stiffness characteristics, to various portions of the shaft 12.

Figure 2:
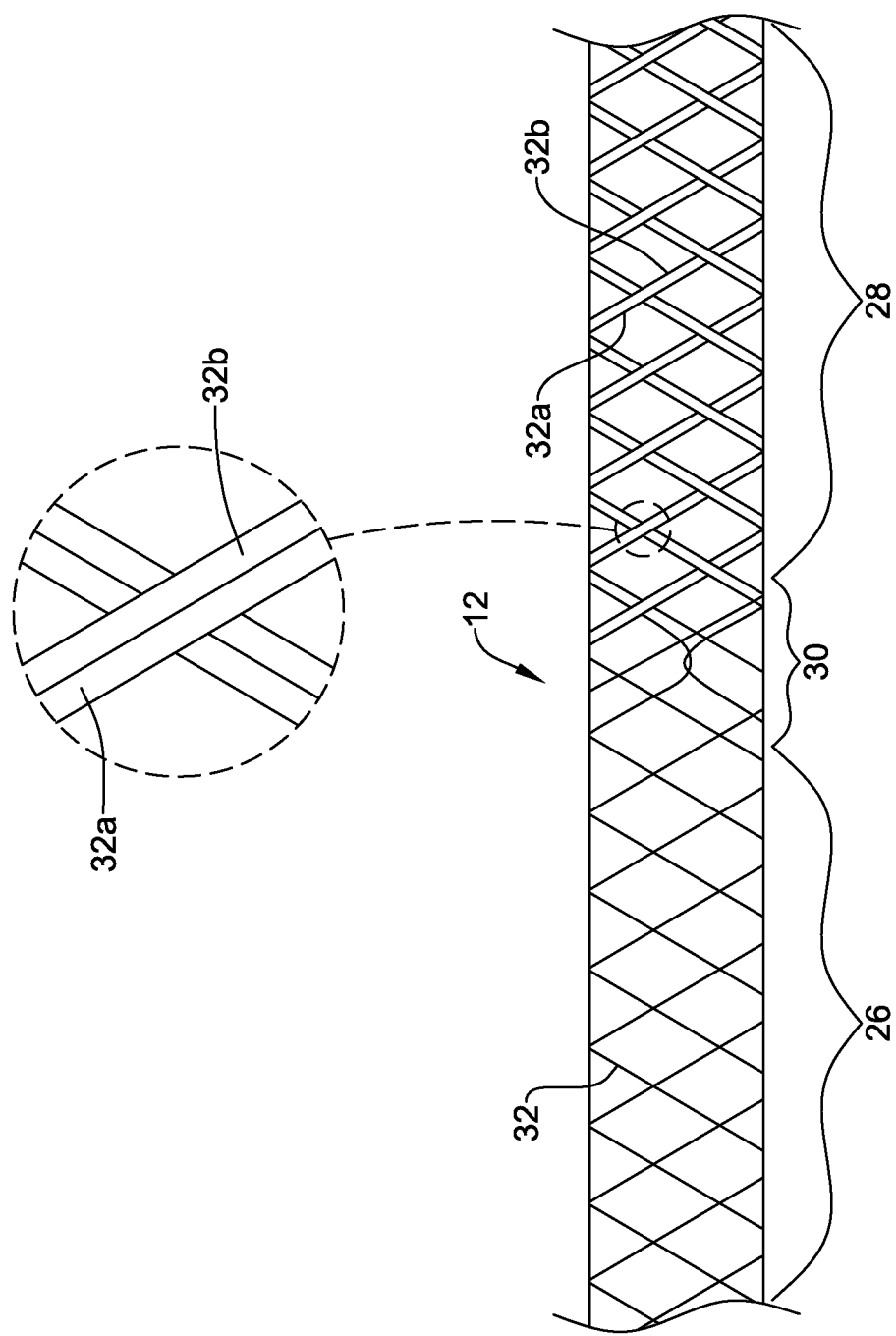
FIG. 2 illustrates a portion of a reinforcing member disposed along the guide catheter of FIG. 1.

FIG. 2 illustrates a portion of the catheter shaft 12 shown in FIG. 1. Specifically, FIG. 2 illustrates a portion of the catheter 10 which includes one or more braided filaments 32 disposed along a portion of the catheter shaft 12. It can be appreciated that FIG. 2 illustrates one or more braided filaments 32 disposed along an outer surface of the catheter shaft 12. However, it can be further appreciated that the one or more braided filaments 32 shown in FIG. 2 may be embedded within the wall of the catheter shaft 12. For example, the one or more braided filaments 32 shown in FIG. 2 may be applied to a first layer of the catheter shaft 12 whereby a second layer is subsequently disposed overtop the first layer, thereby embedding the one or more braided filaments 32 between two (or more) layers of the catheter shaft 12.

FIG. 2 further illustrates that the catheter shaft 12 may include a first braided region 26 having a plurality of braided filaments 32 extending therealong, a second braided region 28 (constructed using the same braided filaments 32 utilized to construct the first braided region 26) and a transition region 30 positioned between the first braided region 26 and the second braided region 28. The transition region may have a length between 0.025 inches and 0.075 inches.

FIG. 2 further illustrates that, in some examples, the pattern of braided filaments in the first braided region 26 may be different from the pattern created by the braided filaments of the second braided region 28. For example, the pattern of braided filaments 32 of the first braided region 26 may be constructed by utilizing two or more filaments braided over and under one another. This type of braid pattern may be referred to as a "diamond pattern," "diamond pattern-half load," and/or a "1 over/1 under" braid pattern. Further, the number of filaments utilized to create the first braided region 26 may include 1, 2, 3, 4, 5, 6, 7, 8, 9, 10, 11, 12, 13, 14, 15, 16 or more filaments. It can be appreciated that a braiding machine may be utilized to braid any number of filaments into the pattern shown in the first braided region 26 of FIG. 2. For example, a braiding machine may be utilized to braid sixteen individual filaments into the "diamond pattern-half load," pattern shown in FIG. 2.

As discussed above (and as FIG. 2 illustrates), in some examples, the braiding pattern illustrated in the first braided region 26 may shift to a different braiding pattern over a portion of the catheter shaft 12. For example, FIG. 2 illustrates that the individual filaments 32 may be continuously looped, wound, braided, reconfigured, etc. within the transition region 30 such that they form a new braid pattern in the second braided region 28. Specifically, FIG. 2 illustrates that the second braided region 28 may include a pattern whereby an individual filament 32 of the first braided region pairs together with another filament 32 of the first braided region 26 to form a pair of filaments 32*a*/32*b*, whereby the individual filaments 32*a*/32*b* run parallel to one another (the detailed view of FIG. 2 illustrates a pair of filaments 32*a*/32*b* running parallel to each other). Further, these "pairs" of filaments may be subsequently braided in a braid pattern referred to as a "diamond pattern-full load" and/or "2 over/2 under" braid pattern. As is shown below in FIG. 8, this braid pattern may be created be braiding "pairs" of filaments with other "pairs" of filaments. It is noted that while FIG. 2 illustrates a two-filament "pair" of filaments (e.g., pairs of two individual filaments) braided with multiple other two-filament "pairs" of filaments, this is not intended to be limiting. Rather, in some examples, "groups" of filaments numbering 3, 4, 5, 6, 7, 8 or more filaments may be grouped together and braided with other groups of filaments having the same or a different number of filaments. For example, a group of eight filaments may be braided in a "diamond pattern-full load" with one or more other distinct groups of filaments (which may or may not have eight individual filaments).

In some examples, the first braided region 26 may include sixteen individual filaments braided in a "diamond pattern-half load" pattern. Further, after transitioning through region 30, the second braided region 28 may include eight "pairs" of filaments braided together in a "diamond pattern-full load" pattern. In other words, each pair of braided filaments in the second braided region 28 may include two individual filaments 32*a*/32*b* which run parallel (and in close proximity) to one another. It can be appreciated that the reference numerals 32*a*/32*b* may identity two example filaments of the plurality of filaments 32 of the first braided region 26. As discussed above, the filaments 32 may run continuously and uninterrupted from the first braided region 26, through the transition region 30 and through the second braided region 28.

Figure 2A:
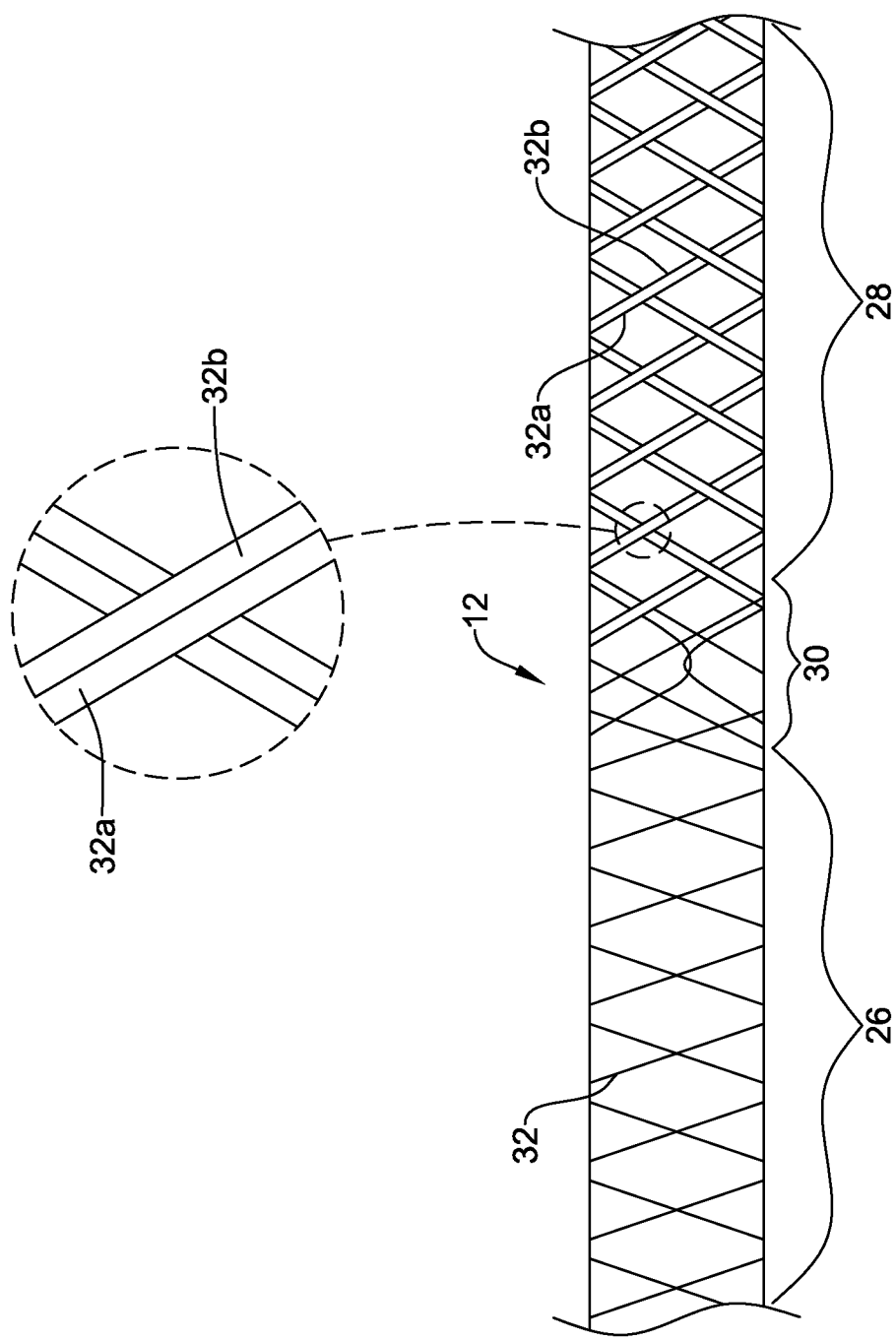
FIG. 2A illustrates another example of a reinforcing member disposed along the guide catheter of FIG. 1.

FIG. 2A illustrates the catheter shaft 12 shown in FIG. 2, including the one or more braided filaments 32 disposed along the first braided region 26. However, FIG. 2A illustrates the braided filaments 32 of the first braided region 26 may have a pitch angle which is greater than the pitch angle depicted by the braided filaments 32 shown in the first braided region 26 of FIG. 2. However, this is not intended to be limiting. Rather, it can be appreciated that the braided filaments 32 of the first braided region 26 of FIG. 2A may have a pitch angle which is less than the pitch angle depicted by the braided filaments 32 shown in the first braided region 26 of FIG. 2.

It can further be appreciated that any of the catheter shaft examples disclosed herein may include regions of braided filaments which have different pitch angles (e.g., two adjacent regions of braided filaments along a single catheter shaft may have different pitch angles). For example, FIG. 2 illustrates that the braided filaments of the first braided region 26 may have substantially the same pitch angle as the braided filaments 32a/32b in the second braided region 28 of FIG. 2. However, FIG. 2A illustrates that the braided filaments 32 shown in the first braided region 26 of FIG. 2A may have a greater pitch angle than the corresponding filaments 32a/32b shown in the second braided region 28 of FIG. 2A. While not illustrated in FIG. 2A, it can be appreciated that the first braided region 26 of FIG. 2A may have a pitch angle which is less than the corresponding filaments 32a/32b shown in the second braided region 28 of FIG. 2A. It can be further appreciated that the various braided regions along any catheter shaft described herein may have similar or different pitch angles.

Figure 3:
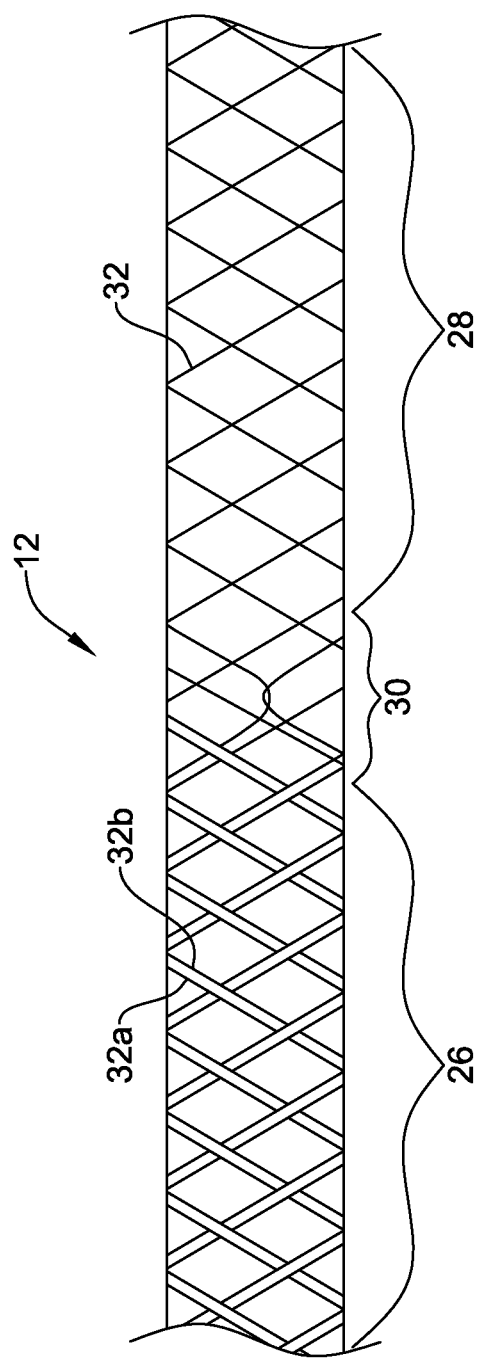
FIG. 3 illustrates a portion of another example guide catheter.

FIG. 3 illustrates the catheter shaft 12 described above. However, FIG. 3 illustrates that, in some examples, the first braided region 26 may include the "diamond pattern-full load" (constructed using pairs of braided filaments as described above) while the second braided region 28 may include the "diamond pattern-half load" (constructed using the same filaments utilized to construct the first braided region 26), as described above. Further, FIG. 3 illustrates the transition region 30 positioned between the first braided region 26 and the second braided region 28. For example, FIG. 3 illustrates the pair of filaments 32a/32b forming a portion of the "diamond pattern-full load" transitioning into the "diamond pattern-half load," having overlapping filaments 32 (whereby the filaments 32a/32b continuously transition into the filaments 32).

Figure 4:
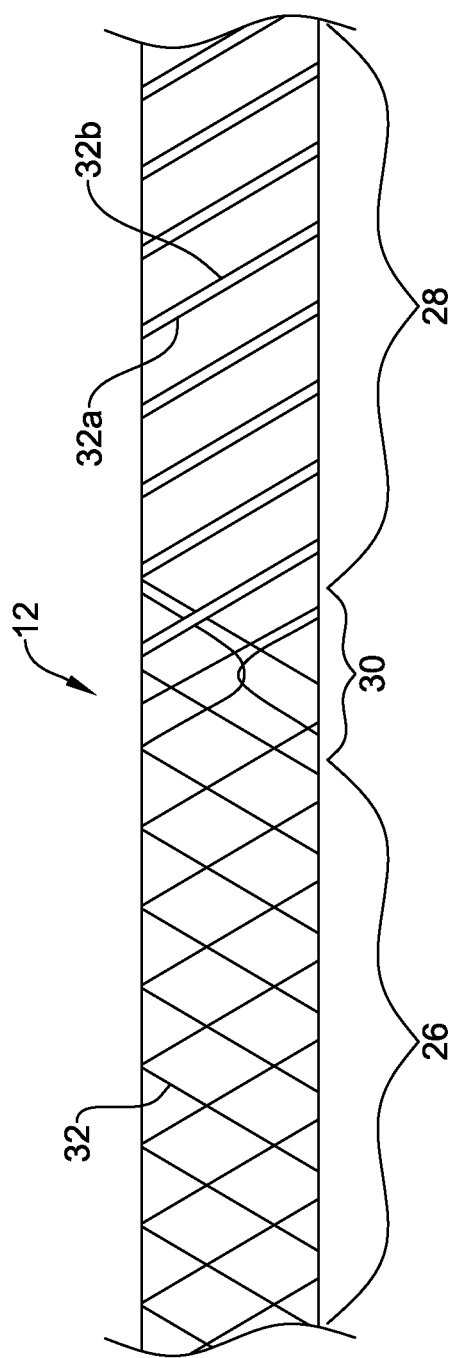
FIG. 4 illustrates a portion of another example guide catheter.

FIG. 4 illustrates the catheter shaft 12 described above. However, FIG. 4 illustrates that, in some examples, the second braided region 28 may include the pairs of filaments (of which filaments 32a/32b form one pair) are formed into a spiral pattern along the second braided region 28. It can be appreciated from FIG. 4 that each individual pair of filaments may be spaced away from one another to form the spiral pattern shown in FIG. 4.

Figure 5:
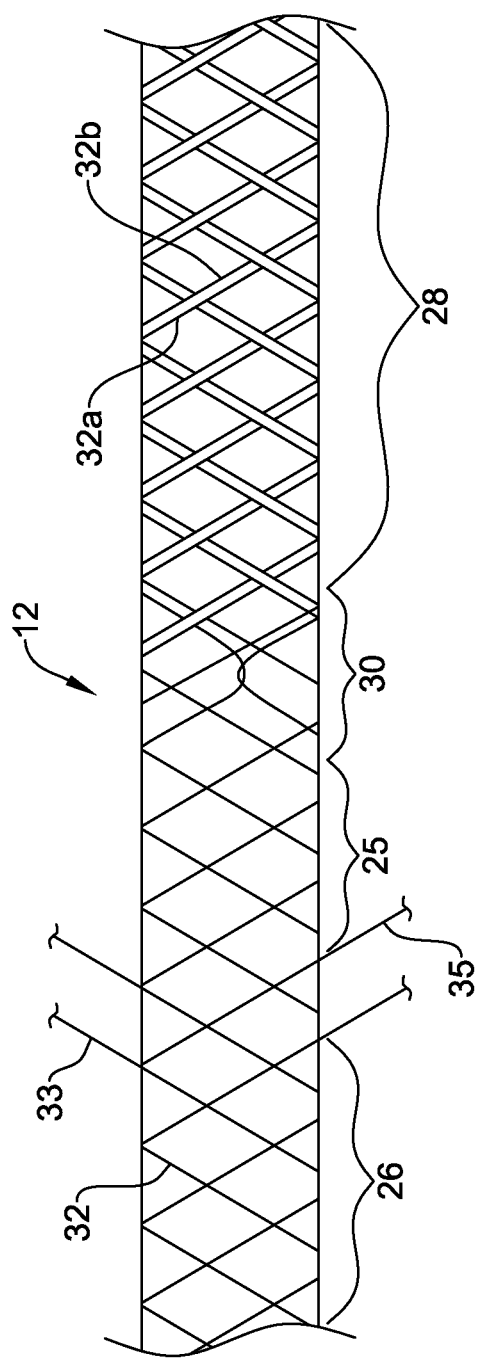
FIG. 5 illustrates an example manufacturing step of an example guide catheter.

FIG. 5 illustrates an example manufacturing method which may be utilized to construct the catheter shaft 12 described above. FIG. 5 illustrates the catheter shaft 12 including the first braided region 26, the second braided region 28 and the transition region 30, as described above. In some examples, a braiding machine may braid the first braided region 26 into a braided pattern (e.g., the "diamond pattern-half load") and reconfigure all of the braided members through the transition region 30 into a new braided pattern (e.g., the "diamond pattern-full load") within the second braided region 28, as described above. For example, the braiding machine may transition sixteen individual filaments 32 within the first braided region 26 into eight pairs of filaments 32a/32b within the second braided region 28.

However, in other examples, the braiding machine may be able to suspend (e.g., pull out, hold out, remove, etc.) one or more filaments from the braiding pattern at a given position along the length of the catheter 12 while still continuing to braid the filaments which have not been pulled out from the pattern. The filaments which are suspended by the braiding machine may be reintroduced into the pattern at a position further downstream from the point at which they were suspended. For example, FIG. 5 illustrates example filaments 33/35 which have been pulled out from the braiding pattern of the first braiding region 26 (the filaments 33/35 are pulled out as the braiding machine moves along the catheter shaft from the first braided region 26 to the second braided region 28).

It can further be appreciated that after the braiding machine pulls out the filaments 33/35, a third braided region 25 may be formed which includes fewer filaments than the first braided region 26. The third braided region 25 may exhibit different performance characteristics than the first braided region 26, the second braided region 28 and/or the transition region 30. For example, the third braided region 25 may be more flexible than the first braided region 26, the second braided region 28 and/or the transition region 30. It should be noted that, in some examples, the suspended filaments 33/35 may be terminated at the point at which they are removed. It can be appreciated that in the examples in which one or more filaments are terminated, the braided regions downstream from that point will not include the terminated filaments (e.g., terminated filaments 33/35).

Figure 6:
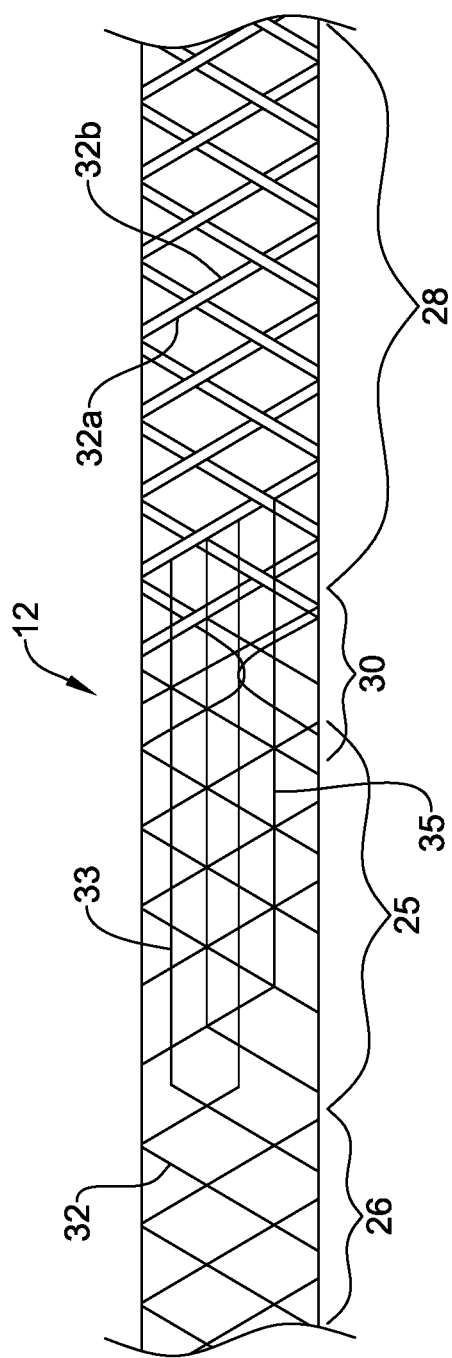
FIG. 6 illustrates another example guide catheter.

However, in other instances, one or more suspended filaments 33/35 may be reintroduced back into the braid at a location along the catheter shaft 12 downstream from where they were pulled out. For example, FIG. 6 illustrates the catheter shaft 12 showing the suspended filaments 33/35 after they have been reintroduced back into the braid. FIG. 6 shows the individual filaments 33/35 laying overtop the third braided region 25 and the transition region 30, prior to being reintroduced back into the second braided region 28.

Figure 7:
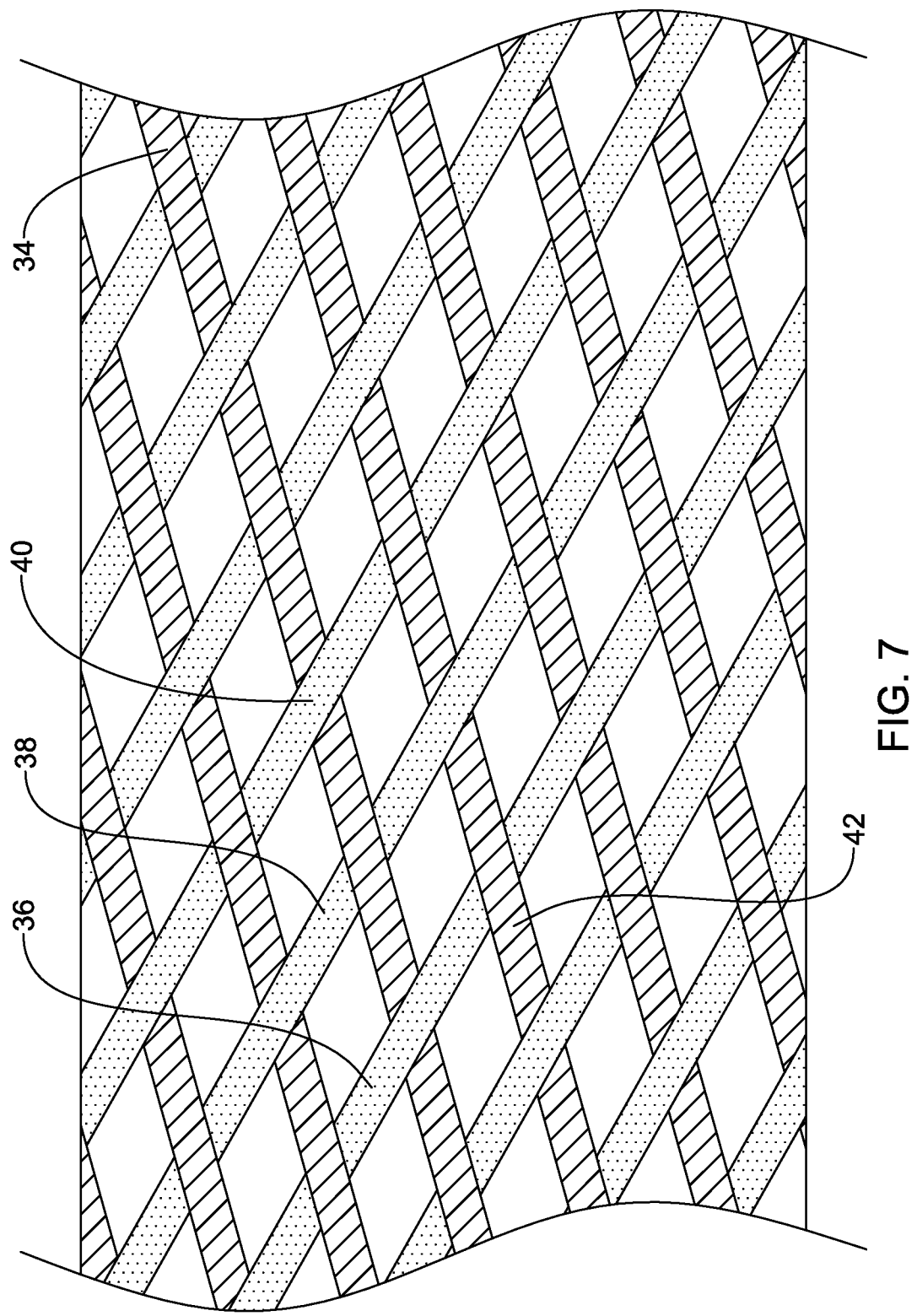
FIG. 7 illustrates an example braid pattern of a reinforcing member.

FIG. 7 illustrates the example "diamond pattern-half load" pattern as described above. This pattern may be formed by an example braiding machine. The "diamond pattern-half load" may be formed along any portion of the catheter shaft 12 and may be positioned adjacent to a variety of other braided regions. FIG. 7 illustrates three example filaments 36/38/40 which run parallel to one another and an example filament 34 which is woven under filament 36, over filament 38 and then under filament 40 in an "under-over-under" pattern. Similarly, FIG. 7 illustrates the filament 42 which runs parallel to the filament 34. FIG. 7 illustrates that the filament 42 is woven over filament 36, under filament 38 and over filament 40 in an "over-under-over" pattern.

Figure 8:
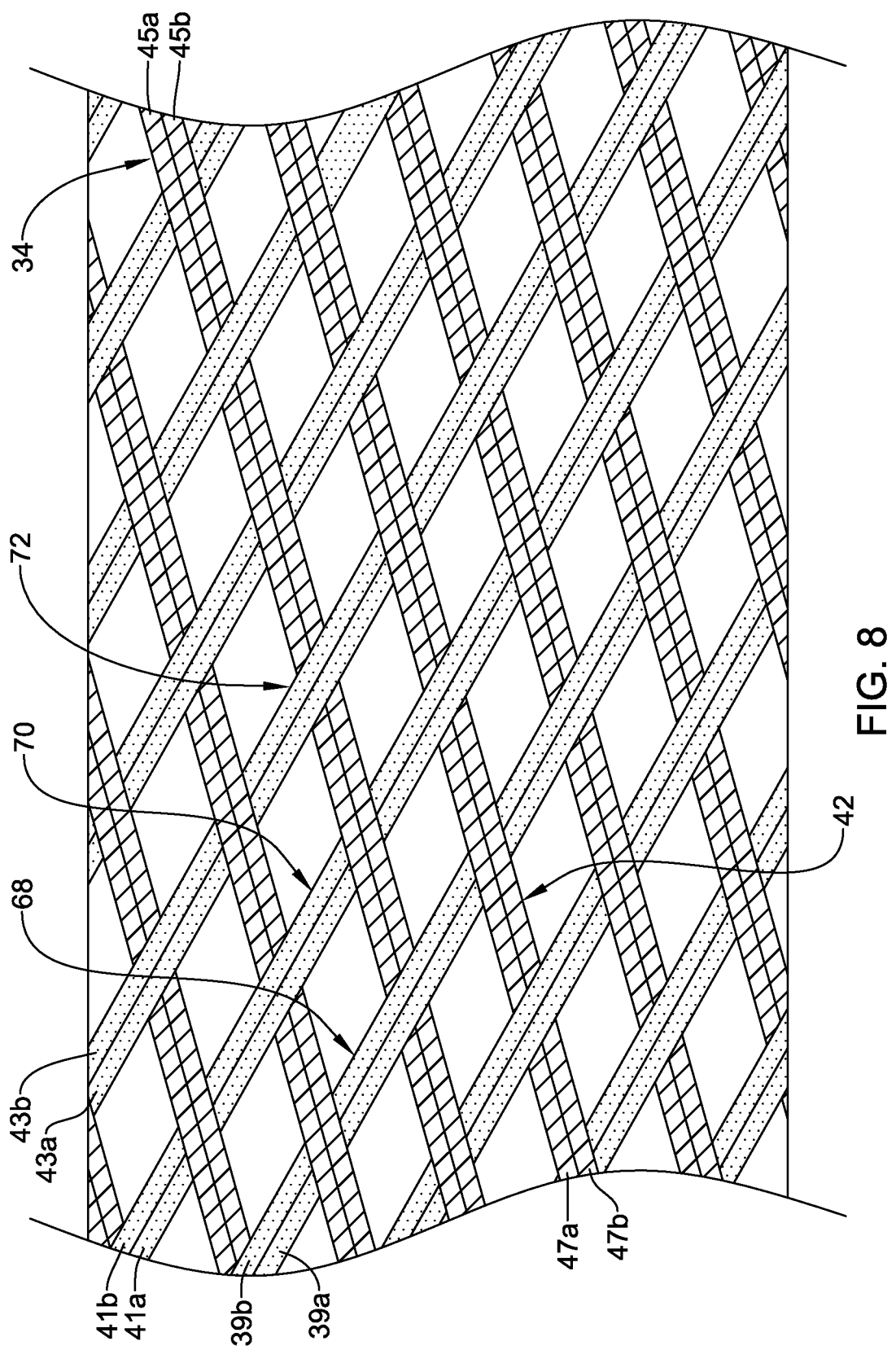
FIG. 8 illustrates another example braid pattern of a reinforcing member.

FIG. 8 illustrates the example "diamond pattern-full load" pattern as described above. This pattern may be formed by an example braiding machine. The "diamond pattern-full load" may be formed along any portion of the catheter shaft 12 and may be positioned adjacent to a variety of other braided regions. To illustrate the interwoven design of the filament pairs to form the "diamond pattern-full load," FIG. 8 illustrates five example "pairs" of filaments 34/42/68/70/72. Each of the pairs of filaments 34/42/68/70/72 are formed from individual filaments running parallel to another filament. For example, filament pair 68 may be formed from individual filaments 39a/39b, filament pair 70 may be formed from individual filaments 41a/41b, filament pair 72 may be formed from individual filaments 43a/43b, filament pair 34 may be formed from individual filaments 45a/45b and filament pair 42 may be formed from individual filaments 47a/47b. FIG. 8 shows filament pairs 68/70/72 woven in an "under-over-under" pattern with filament pairs 34/42 to form a portion of the "diamond pattern-full load" illustrated in FIG. 8.

Figure 9:
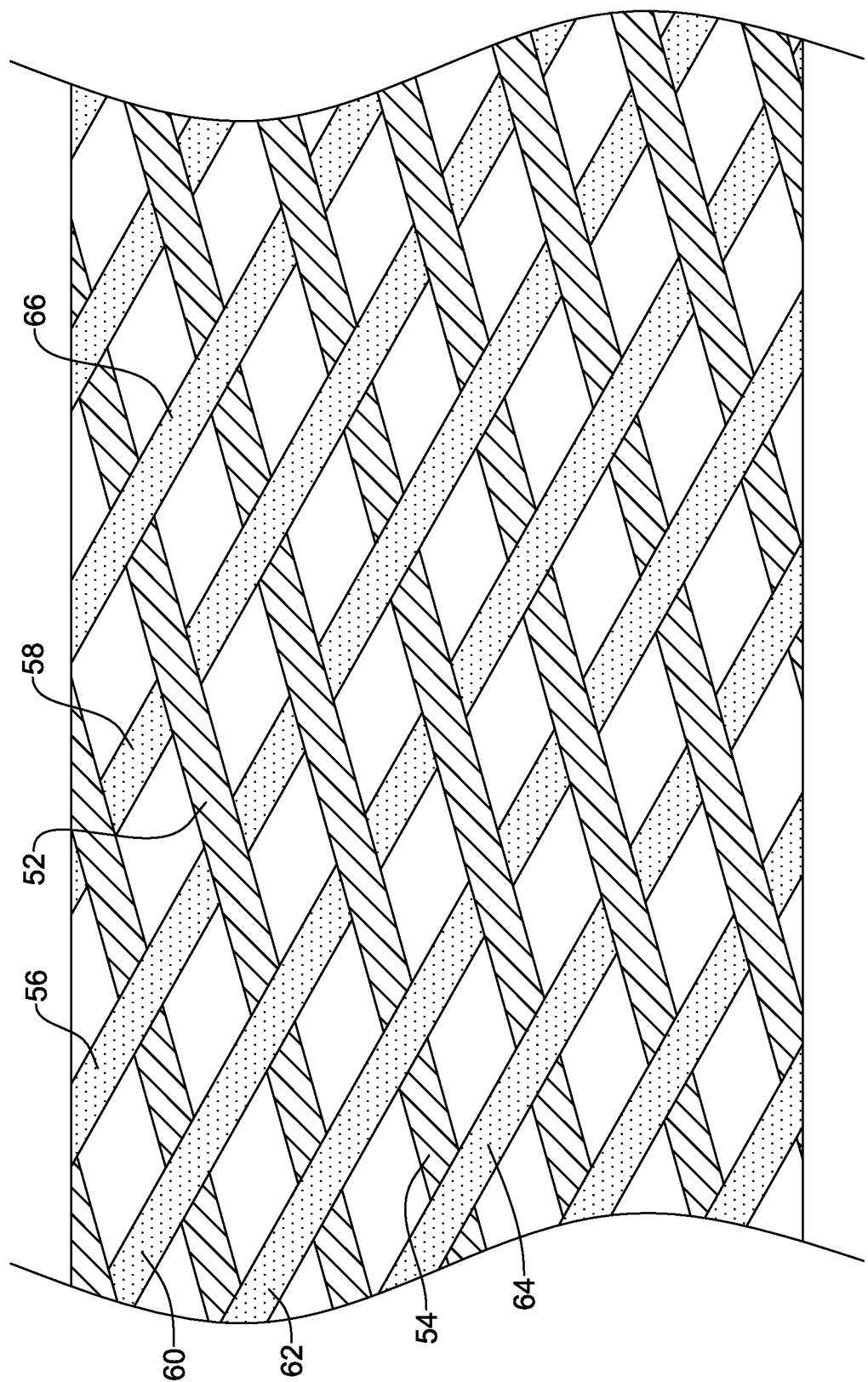
FIG. 9 illustrates another example braid pattern of a reinforcing member.

FIG. 9 illustrates another example braid pattern which may be referred to as a "herringbone pattern." This pattern may be formed by an example braiding machine. The "herringbone pattern" may be formed along any portion of the catheter shaft 12 and may be positioned adjacent to a variety of other braided regions. To illustrate the interwoven design of the filament pairs to form the "herringbone pattern," FIG. 9 illustrates four example filaments 52/56/58/66 which are interwoven with four other example filaments 54/60/62/64 to form a portion of the "herringbone pattern" illustrated in FIG. 9.

The materials that can be used for the various components of catheter 10 and the various tubular members disclosed herein may include those commonly associated with medical devices.

Catheter 10 and/or other components of catheter 10 may be made from a metal, metal alloy, polymer (some examples of which are disclosed below), a metal-polymer composite, ceramics, combinations thereof, and the like, or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex® high-density polyethylene, Marlex® low-density polyethylene, linear low density polyethylene (for example REXELL®), Ultra High Density polyethylene, crosslinked polyethylene, polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments the sheath can be blended with a liquid crystal polymer (LCP). For example, the mixture can contain up to about 6 percent LCP.

Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

In at least some embodiments, portions or all of catheter 10 may also be doped with, made of, or otherwise include a radiopaque material. Radiopaque materials are understood to be materials capable of producing a relatively bright image on a fluoroscopy screen or another imaging technique during a medical procedure. This relatively bright image aids the user of catheter 10 in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of catheter 10 to achieve the same result.

In some embodiments, a degree of Magnetic Resonance Imaging (MRI) compatibility is imparted into catheter 10. For example, catheter 10, or portions thereof, may be made of a material that does not substantially distort the image and create substantial artifacts (e.g., gaps in the image). Certain ferromagnetic materials, for example, may not be suitable because they may create artifacts in an MRI image. Catheter 10, or portions thereof, may also be made from a material that the Mill machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The disclosure's scope is, of course, defined in the language in which the appended claims are expressed.

What is claimed is:
1. A medical device, comprising:
   an elongate member having a proximal end region, a distal end region and an outer surface;
   a plurality of filaments braided together in a first braided pattern along a first braided region of the elongate member, wherein the plurality of filaments extend continuously to a second braided region along the elongate member, wherein the plurality of filaments along the second braided region form a second braided pattern different from the first braided pattern;
   wherein a first filament of the plurality of filaments extends along the first braided region in a first rotational direction, and wherein the first filament of the plurality of filaments extends along the second braided region in a second rotational direction different from the first rotational direction, and wherein the first filament changes rotational direction from the first rotational direction to the second rotational direction along a transition region positioned between the first braided region and the second braided region;
   wherein a first filament of the plurality of filaments extends parallel to a second filament of the plurality of filaments to form a first pair of filaments in the second braided region, and wherein the first filament is in a first proximity relative to the second filament;

wherein a third filament of the plurality of filaments extends parallel to a fourth filament of the plurality of filaments to form a second pair of filaments in the second braided region, and wherein the third filament is in a second proximity relative to the fourth filament;

wherein the first pair of filaments is interwoven with the second pair of filaments in the second braided region; and wherein the first pair of filaments is in a third proximity relative to the second pair of filaments, and wherein the third proximity is different from the first proximity and the second proximity.

2. The medical device of claim 1, wherein the plurality of filaments continuously transition from the first braided pattern to the second braided pattern along the transition region.

3. The medical device of claim 1, wherein the filaments forming the first braided pattern are interwoven in a diamond-half load braid pattern.

4. The medical device of claim 1, wherein the filaments forming the first braided pattern are interwoven in a herringbone braid pattern.

5. The medical device of claim 1, wherein the plurality of filaments of the first braided region define a first pitch angle, and wherein the plurality filaments of the second braided region define a second pitch angle different from the first pitch angle.

6. The medical device of claim 1, wherein the third proximity is greater than the first proximity and the second proximity.

7. The medical device of claim 1, wherein the first proximity defines that the first filament is touching the second filament and wherein the second proximity defines that the third filament is touching the fourth filament.

8. The medical device of claim 1, wherein the first pair of filaments is interwoven with the second pair of filaments in diamond-full load braid pattern.

9. The medical device of claim 1, wherein the plurality of filaments are disposed along the outer surface of the elongate tubular member.

10. The medical device of claim 2, wherein the transition region includes a length between 0.040 inches and 0.060 inches.

11. A guide catheter, comprising:
an elongate shaft having a lumen, an outer surface and a plurality of reinforcing wires disposed along the outer surface;
wherein the plurality of reinforcing wires are interwoven in a first braided pattern along a first braided region of the elongate shaft, and wherein the plurality of reinforcing wires extend continuously to a second braided region, and wherein the plurality of reinforcing wires of the second braided region form a second braided pattern different from the first braided pattern;
wherein a first filament of the plurality of filaments extends along the first braided region in a first rotational direction, and wherein the first filament of the plurality of filaments extends along the second braided region in a second rotational direction different from the first rotational direction, and wherein the first filament changes rotational direction from the first rotational direction to the second rotational direction along a transition region positioned between the first braided region and the second braided region;

wherein a first wire of the plurality of wires extends parallel to a second wire of the plurality of wires to form a first pair of wires in the second braided region, and wherein the first wire is in a first proximity relative to the second wire;

wherein a third wire of the plurality of wire extends parallel to a fourth wire of the plurality of wires to form a second pair of wires in the second braided region, and wherein the third wire is in a second proximity relative to the fourth wire; and wherein the first pair of wires is in a third proximity relative to the second pair of wires, and wherein the third proximity is different from the first proximity and the second proximity.

12. The guide catheter of claim 11, wherein the plurality of reinforcing wires continuously transition from the first braided pattern to the second braided pattern along the transition region.

13. The guide catheter of claim 11, wherein the reinforcing wires forming the first braided pattern are interwoven in a diamond-half load braid pattern.

14. The guide catheter of claim 11, wherein the reinforcing wires forming the first braided pattern are interwoven in a herringbone braid pattern.

15. The guide catheter of claim 11, wherein the third proximity is greater than the first proximity and the second proximity.

16. The guide catheter of claim 11, wherein the first proximity defines that the first wire is touching the second wire and wherein the second proximity defines that the third wire is touching the fourth wire.

17. The guide catheter of claim 11, wherein the first pair of wires is interwoven with the second pair of wires in the second braided region.

18. The guide catheter of claim 17, wherein the first pair of wires is interwoven with the second pair of wires in a diamond-full load braid pattern.

19. A medical device, comprising:
an elongate member having a proximal end region, a distal end region and an outer surface;
a plurality of filaments extending continuously along the elongate member, wherein the plurality of filaments are braided together in a first braided pattern along a first braided region of the elongate member, a second braided pattern along a second braided region of the elongate member, and a third braided pattern along a transition region of the elongate member, wherein the transition region is positioned between the first braided region and the second braided region;
wherein a first filament of the plurality of filaments is separated from a second filament of the plurality of filaments along the first braided region; and
wherein the first filament of the plurality of filaments extends parallel to the second filament of the plurality of filaments to form a first pair of wires in the second braided region; and
wherein the first filament of the plurality of filaments is touching the second filament of the plurality of filaments along the second braided region.

* * * * *